(12) United States Patent
Kroger

(10) Patent No.: US 8,249,307 B2
(45) Date of Patent: Aug. 21, 2012

(54) EVALUATION OF MEAT TENDERNESS

(75) Inventor: Chris Kroger, Lower Hutt (NZ)

(73) Assignee: Institute of Geological and Nuclear Sciences, Ltd., Lower Hutt (NZ)

( * ) Notice: Subject to any disclaimer, the term of this patent is extended or adjusted under 35 U.S.C. 154(b) by 778 days.

(21) Appl. No.: 12/226,700

(22) PCT Filed: Apr. 26, 2007

(86) PCT No.: PCT/NZ2007/000092
§ 371 (c)(1),
(2), (4) Date: May 1, 2009

(87) PCT Pub. No.: WO2007/123427
PCT Pub. Date: Nov. 1, 2007

(65) Prior Publication Data
US 2009/0310826 A1    Dec. 17, 2009

(30) Foreign Application Priority Data

Apr. 26, 2006  (NZ) .................................. 546808

(51) Int. Cl.
*G06K 9/00* (2006.01)
*G01N 23/06* (2006.01)
*G01N 23/201* (2006.01)
(52) U.S. Cl. ..................... 382/110; 378/53; 378/88
(58) Field of Classification Search ............... 382/110; 378/53, 88
See application file for complete search history.

(56) References Cited

U.S. PATENT DOCUMENTS

| 6,198,834 B1 | 3/2001 | Belk et al. |
| 6,449,334 B1 | 9/2002 | Mazess et al. |

FOREIGN PATENT DOCUMENTS

| CA | 1067806 | 12/1979 |
| EP | P123729 | 8/2011 |
| WO | WO 00/49400 | 8/2000 |
| WO | 01/96844 A1 | 6/2001 |
| WO | WO 01/96844 | 12/2001 |

OTHER PUBLICATIONS

Jeyamkondan, "Predicting beef tenderness using x-ray attenuation properties", Non destructive evaluation of beef palatibility—Thesis (PhD), 2004, Chapter IX, pp. 192-207, XP002653413, Oklahoma State University).*
Predicting Beef Tenderness Using Dual Energy X-ray Absorption—Jun. 16, 2003.
Predicting Beef Tenderness Using X-ray Attenuation Properties—Mar. 8, 2004.
Tenderness Classification of Beef: 1. Evaluation of Beef Longisimus Shear Force at 1 or 2 Days Postmortem as a Predictor of Aged Beef Tenderness—Sep. 1, 1997.
Using Objective Measures of Muscle Color to Predict Beef Longisimus Tenderness—Jan. 1, 1997.

* cited by examiner

*Primary Examiner* — Vu Le
*Assistant Examiner* — Amara Abdi
(74) *Attorney, Agent, or Firm* — Thomas R. Vigil

(57) ABSTRACT

The method and apparatus for estimating the tenderness of meat comprises scanning a sample of meat through an x-ray beam; detecting or measuring the transmitted x-ray radiation through the meat sample; relating the transmitted x-ray radiation to a characteristic of the shear force of the meat sample; and assessing the tenderness of the meat sample from the characteristic of the shear force.

17 Claims, 6 Drawing Sheets

EVALUATION OF MEAT TENDERNESS

FIELD OF INVENTION

The invention relates to evaluation of meat tenderness. More particularly but not exclusively it relates to the automatic objective evaluation of meat tenderness by an x-ray scanner.

BACKGROUND

Meat tenderness describes primarily the force required to bite through a sample of meat, with more tender meat generally being more desirable. Tenderness factors strongly in determining overall palatability, and extensive tenderness research is ongoing worldwide (see for instance Hopkins D. L., and J. M. Thompson, 2002. Factors contributing to proteolysis and disruption of myofibrillar proteins and the impact on tenderization in beef and sheep meat. Australian Journal of Agricultural Research, 53, 149-166; Purchas, R. W., 1990. An assessment of the role of pH differences in determining the relative tenderness of meat from bulls and steers, Meat Science, 27, 129-140; Purchas, R. W., R. Aungsupakorn, 1993. Further investigations into the relationship between ultimate pH and tenderness for beef samples from bulls and steers, Meat Science, 34, 163-178; Watanabe, A., C. C. Daly and C. E. Devine, 1996. The effects of the ultimate pH of meat on tenderness changes during aging, Meat Science, 42(1), 67-78). So far non-invasive efforts to determine tenderness prior to consumption have met with limited success. Many official meat grading systems appraise visible parameters such as marbling as a predictor of tenderness, but they actually provide only a poor indication of tenderness. (Seideman, S. C., M. Koohmaraie, & J. D. Crouse, 1987. Factors associated with tenderness in young beef, Meat Science, 20(4), 281-291; Li, J., J. Tan, F. Martz, & H. Heimann, 1999. Image texture features as indicators for beef tenderness, Meat Science, 53, 17-22; Li, J., J. Tan, & P. Shatadal, 2001. Classification of tough and tender beef by image texture analysis, Meat Science, 57, 341-346).

An objective measure of tenderness is the shear force, determined with the Warner-Bratzler or the MIRINZ shear force devices under strict adherence to standardized procedures (Wheeler, T. L., Shackelford, S. D., Johnson, L. P., Miller, M. F., Miller, R. M. & Koohmaraie, M. 1997. A comparison of Warner Bratzler shear force assessment within and among institutions. J. Animal Science, 75, 2423-2432). Following guidelines the shear force can be determined accurately (Bekhit, A. E. D., Devine, C. E., Morton, J. D., Bickerstaffe, R., 2003. Towards unifying meat shear force measurement systems to determine meat tenderness. Proc. 49$^{th}$ Int. Congress of Meat Science & Technology, Buenos Aires, Brazil), but strong within-muscle variations exist that are poorly explained (Alsmeyer, R. L., J. W. Thornton and R. L. Hiner, 1965. Some dorsal-lateral location tenderness differences in the longissimus dorsi muscle of beef and pork. J. Animal Science 24, 526-530; Gariépy, C., S. D. M. Jones and W. M. Robertson, 1990. Variation in meat quality at three sites along the length of the beef longissimus muscle. Canadian Journal of Animal Science, 70, 707-710). Thus, unless a representative average is presented the shear force should be cautiously compared with other methods. A method that provides an overall or average tenderness value is also more useful for the consumer.

Shear force is the force required to cut through a sample of meat. The force applied to the meat varies as the blade cuts through the sample. First there will be an elastic deformation of the meat until the blade severs the tissue. The force applied until the blade actually shears the meat sample is the initial yield. The blade will then be required to apply a varying force to move through the meat sample at a constant speed. The maximum force required for cutting the meat sample is the peak force. The mean shear force is the average over all encountered forces applied while cutting the meat sample.

Imaging offers the most promising way to replace human visual assessment and random laboratory testing. Some researchers used visible light: for example Li et al. (1999); Li et al. (2001) (full references above); and Tan(Tan, J., 2004. Meat quality evaluation by computer vision, J. Food Eng., 61, 27-35), where in the latter a correlation between muscle texture and peak shear force has been reported, however the correlation was weak at $R^2=0.34$. Near infrared spectroscopy has been used with some success. For example, see McGlone, V. A., Devine, C. E., Wells, R. W., 2005. Detection of tenderness, post rigor age and water status changes in sheep using near infrared spectroscopy, J. Near Infrared Spectroscopy, 13, 277-285; Devine, C. E. and McGlone V. A. 1998. On-line assessment of meat tenderness. Proc. 44th Int. Congress of Meat Science and Technology, Barcelona, 958-959; Park, B., Y. R. Chen, W. R. Hruschka, S. D. Shackelford, M. Koohmaraie, 1998. Near-infrared reflectance analysis for predicting beef longissimus tenderness, J. Animal Science, 76, (8), 2115-2120; and Liu, Y., B. G. Lyon, W. R. Windham, C. E. Realini, T. D. Pringle and S. Duckett, 2003. Prediction of color, texture, and sensory characteristics of beef steaks by visible and near infrared reflectance spectroscopy. A feasibility study. Meat Science, 65, (3), 1107-1115. Better results were generally achieved when an approximate and arbitrary classification sufficed (i.e. tough, medium, and tender), rather than on the use of a precise scale.

Dual energy x-ray absorptiometry (DEXA) already has applications in the primary industry (C. Kröger, C. M. Bartle, J. G. West, 2004. Non-invasive measurements of wool and meat properties, Proc. 18th Int. NDT, Montreal, Canada; Bartle, C. M., C. Kroger, and J. G. West, 2004. New uses of x-ray transmission techniques in the animal-based industries. Rad. Phys. Chem., 71, 843-851). Based on a crude tenderness scale a correlation was found between tenderness and x-ray images (PCT International Patent Application No. PCT/NZ01/00108 which is incorporated herein by reference). In this approach, the pre-processed false colour x-ray images created in an airport security DEXA scanner were separated into their red, green, and blue layers and the intensity from each layer was correlated to assumed tenderness depending on the type of cut, where a tenderloin steak was considered most tender and rib eye steak less tender and so on. The investigation revealed a distinct correlation based on the arbitrary scale. There were a number of disadvantages with this technique however. Firstly, the method was based on images pre-processed using proprietary software. Secondly, false colours are based on composition of the object, and while composition may contribute to tenderness, it remains constant over time while tenderness varies (for example with aging of the meat). Thus, the earlier technique may fail for investigation of variation of tenderness over time.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

OBJECT OF THE INVENTION

It is an object of the present invention to provide an improved or alternative method to determining tenderness of consumable meat non-invasively, or at least provide the public with a useful choice.

SUMMARY OF THE INVENTION

In broad terms the invention comprises a method for assessing the tenderness of meat comprising the steps of:
- scanning a sample of meat through an x-ray beam;
- detecting or measuring the transmitted x-ray radiation through the meat sample;
- relating the transmitted x-ray radiation to a characteristic of the shear force of the meat sample;
- assessing the tenderness of the meat sample from the characteristic of the shear force.

Preferably the step of relating the transmitted x-ray radiation to a characteristic of the shear force of the meat sample is via a calculation of the characteristic of shear force, estimation of the characteristic of shear force or comparison with a previously determined characteristic of the shear force.

Preferably the characteristic of shear force is one or more of the shear force, the standard deviation of the shear force, the peak shear force, the mean shear force and the initial yield.

In one preferred embodiment the method includes a pre-step of calibrating the x-ray scanner by correlating images to the measured shear force of the sample or of a representative sample.

Preferably the meat is scanned using a dual energy x-ray absorption scanner to produce two images or arrays of values representative of the intensities of the x-rays at two energy levels.

Preferably the two images or arrays of values comprise a high energy image or array and a low energy image or array.

Preferably the high energy and low energy images or arrays are applied in such a way to calculate the objective tenderness expressed as shear force.

Preferably the high and low energy images or arrays are applied via a regression equation of the general form:

$$PF = A \cdot f'(I_L, I_H) + B \cdot f''(\text{stdev}(r(I_L, I_H))) + C \cdot f'(I_L) + D \cdot f^p(I_H) + E. \quad (1)$$

where:
- PF=the predicted peak force;
- A, B, C, D, and E are constants; and
- m, n, l, and p are integers.

Preferably the regression equation is applied and/or derived in the calibration step.

The equation was found using regression analysis, where x-ray images of meat of known shear force were correlated to the measured shear force values. The equation was to be found in a best fit way, and as a result is a multiple non-linear parameter equation.

In one embodiment the peak shear force is determined (as above).

In an alternative embodiment the mean shear force is determined.

In a further alternative embodiment the initial yield is determined.

Preferably the meat is x-ray scanned in raw state, preferably at temperatures above freezing. Alternatively the meat is scanned in a cooked state. Alternatively or additionally the meat is scanned in a frozen state.

Preferably the size of the meat is of optimum size with respect to the x-ray scanner configuration. The optimum is defined as the largest difference between the high and low energy attenuation as a function of the sum of the two factors.

The method can be used on individual pieces of meat or on a container of meat, providing an averaged result over the entire contents.

Preferably the method may include the step of correcting the assessment for instrumental effects that may affect the assessment of the tenderness.

The images or arrays of values may also be stored for future retrieval and/or processing.

It will be appreciated by those skilled in the art that while the description mentions only x-ray devices gamma ray devices could alternatively be used. The use of the word x-ray throughout the specification should not be taken as limiting but instead be read as including gamma rays and gamma ray devices.

In broad terms in a further aspect the invention includes an apparatus for assessing the tenderness of meat comprising an x-ray source and detector, and an associated computer system arranged to process the output to determine the tenderness (preferably expressed as shear force) of the meat (whether peak, mean or initial yield) and to calculate or assess the tenderness of the meat.

Preferably the apparatus comprises or includes a dual energy x-ray absorption scanner for scanning the meat and arranged to produce two images or arrays of values representative of the intensities if the x-rays at two energy levels.

The apparatus of the invention may also be arranged to store the images or arrays of values for future retrieval and/or processing.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification and claims means "consisting at least in part of"; that is to say when interpreting statements in this specification and claims which include "comprising", features, other than those prefaced by this term in each statement, can also be present. Related terms such as "comprise" and "comprised" are to be interpreted in similar manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF DRAWINGS

The invention will now be described by way of example only and with reference to the drawings in which.

DETAILED DESCRIPTION OF THE INVENTION

DEXA technology has previously been used to investigate tenderness and other properties of meat (see PCT International Patent Application No. PCT/NZ01/00108). However, these techniques required the use of an arbitrary calibration scale. To create the calibration scale a tender piece of meat was scanned and this meat was set as a benchmark to which later scans were compared. Similarly a more tough section of meat was scanned and set as a less tender benchmark.

The preferred embodiment of the current invention differs from the previous uses of DEXA technology in that it uses the peak shear force as an objective scale for comparison. Further the peak shear force is correlated to the unprocessed x-ray images. The mean shear force and the initial yield could also be used, provided the same measurement is used consistently throughout the method.

The preferred method of the invention requires raw meat samples. However, it is possible that cooked and/or frozen meat samples could alternatively be used within the scope of the invention.

Dual Energy X-Ray Absorptiometry (DEXA)

Figure 1:
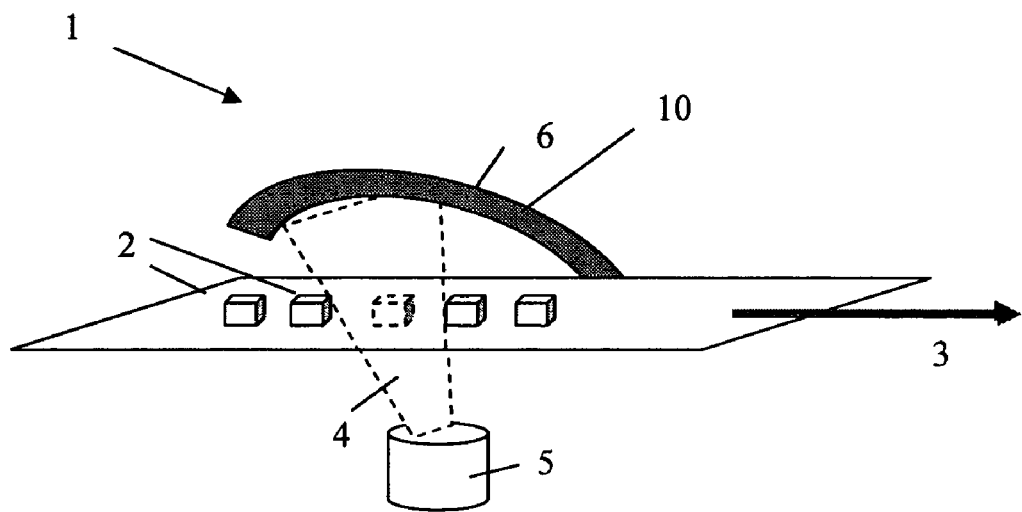
FIG. 1 is a schematic drawing of a principal layout of dual energy x-ray absorption (DEXA) scanner.

FIG. 1 shows a schematic of a layout of a DEXA scanner arrangement that can be used in the invention. The relative location of the principal parts may be different in various models as would be appreciated by one skilled in the art.

A conveying system 1 transports objects (meat samples) 2 in the conveying direction 3 through a usually fan-shaped, preferably collimated, x-ray beam 4 from an x-ray generator 5. The attenuated x-ray signal will be recorded at the x-ray detector array 6 (made up of a plurality of detectors 10 shown in FIG. 2) which is dual energy capable. A digital x-ray image is acquired by moving the object 2 through the fan-shaped x-ray beam 4, while recording the attenuated signal as shown in FIG. 1.

The size of the individual detectors 10 in a given detector array 6 determines the resolution of the image. The attenuated x-ray signal is averaged over the detector area. The resolution perpendicular to the direction of motion is fully fixed with the size of the detector 10, while the pixel size parallel to the moving direction 3 is determined by the conveying speed and the read-out frequency of the detector array 6. A typical detector resolution is about 1 mm².

Figure 2:
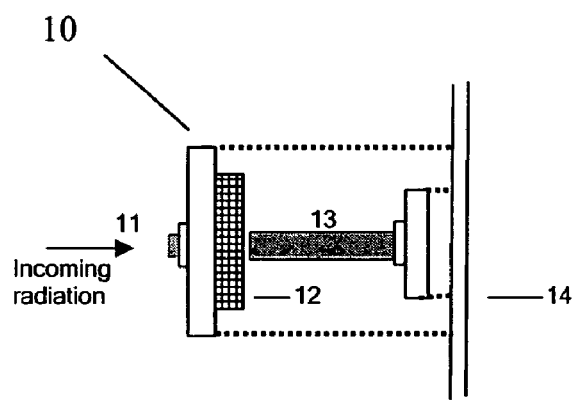
FIG. 2 is a schematic of a dual energy sensitive detector.

FIG. 2 shows a dual energy sensitive detector 10. The detector array 6 of FIG. 1 contains several hundred dual energy capable detectors 10. A low energy detector (LED) 11 with connected electronic attenuation and data transmission parts is located in front of a filter plate 12. The filter plate 12 removes the lower energy part of the x-ray spectrum. A high energy detector element (HED) 13 is illustrated, with its electronic accessories. Dotted lines show electronic data paths towards the main processor unit 14 to the right of the Figure. Note that other ways of obtaining dual energy x-ray images may be feasible, such as alternating x-ray sources and/or offset detectors.

As illustrated, each detector comprises two detector elements. The low energy detector 11 receives the full, attenuated spectrum. Energies below a certain threshold are filtered out after transmission through the low energy detector 11 leaving an x-ray spectrum of a higher mean energy. The high energy, attenuated spectrum is recorded at the second detector 13.

FIG. 2 shows only one detector for dual energy x-ray detecting. Other dual energy x-ray detectors may also be used.

The x-ray image is a data array of intensities I (or grey values) resulting from an object's effective atomic number and thickness, and x-ray emitted intensity and energy. The fundamental law of intensity attenuation (e.g. Benenson, W., J. W. Harris, H. Stocker, H. Lutz, 2002. Handbook of Physics, Springer Verlag New York, p. 961) is $$I=I_0 e^{-\mu' t}, \quad (2)$$

where:
$I_0$ is the non-attenuated intensity,
$\mu'$ is the linear attenuation coefficient, and
t is the thickness of the transmitted object.

To obtain meaningful results the thickness or the attenuation coefficient need to be known, but often neither is identified. By involving images taken at two (or more) mean x-ray energies, the thickness dependence can be cancelled out and information on composition partition given. Solving the exponential law of attenuation of a dual-energy, binary mixture system for the mass fraction of one of the components, the mass fraction of compound 1 in a binary mixture $\omega_1 = 1 - \omega_2$ will be proportional to the following factor:

$$LR = \frac{\ln I_I / I_L}{\ln I_I / I_H} \quad (3)$$

where:
$I_I$ is the incident intensity of the x-ray beam,
$I_L$ is the low energy intensity, and
$I_H$ is the high energy intensity.

LR is called the log-ratio and its derivation was explained in detail for instance by Bartle, C. M., 1995. Features of the measurement of fat in meat using the neutron/gamma transmission (NEUGAT) method. Appl. Radiat. Isot., 46 (5), 741-750; Bartle, C. M., 1999. Comparison of the response of raw wool to simultaneous neutron and γ-ray (neugat) transmission and simultaneous dual energy γ-ray (gamgat) transmission, Appl. Radiat. Isot. 50, 859-866; and Kröger, C., C. M. Bartle, J. G. West, B. vanRensburg, 2006. Wool Base determination using dual energy x-ray absorptiometry (DEXA), Appl. Rad. Isot., in press. The LR is related to composition, which can be assumed to remain constant while mechanical tenderness changes over time under certain circumstances (for example, aging). The variation of composition, expressed in the standard deviations of LR, was used to correlate DEXA and mechanical tenderness. The variation of LR may offer insight into the textural properties of meat, which affect tenderness.

Simple linear regressions of individual DEXA parameters (such as LR and other combinations of both images and their standard deviations) on shear values were calculated, followed by multiple regressions on several DEXA parameters, both in linear and non-linear ways. Although standard deviations were the focal point of the analysis, further parameters were added systematically on a best fit basis. The final prediction equation was selected based on the best multiple correlation coefficient and visual impact in the resulting scatter plot. Regression equations took the general form of:

$$PF = A \cdot f^m(I_L, I_H) + B \cdot f^n(\text{stdev}(r(I_L, I_H))) + C \cdot f^l(I_L) + D \cdot f^p(I_H) + E. \quad (1)$$

where:
PF is the predicted peak force;
A, B, C, D, and E are constants; and
m, n, l, and p are integers.

In use a sample or samples of meat are scanned through an x-ray scanner such as that shown in FIG. 1. The samples pass through an x-ray beam and the attenuated x-rays are detected or measured by detectors. The detected or measured x-rays are related to the shear force of the meat sample. Finally the tenderness of the meat sample is assessed from the shear force.

In preferred embodiments the x-ray scanner is a DEXA scanner. The DEXA scanner provides two images or arrays of values representing a high energy and a low energy x-ray energies. However single or multiple x-ray scanners may be used. Using x-ray scanners with multiple energy detectors allows more information to be provided about the meat being scanned and a more accurate assessment of tenderness to be made. Equation 1 can be expanded to take account of more x-ray energy variables as required.

The step of relating the detected or measured x-rays to the shear force may be by calculation or the shear force, estimation of the shear force or by comparison with a previously determined shear force. For example calculation or estimation of the shear force may involve the regression equation above with suitable constants. The constants for the regression equation may be derived during a calibration step where at least one sample with known shear force is scanned using the x-ray scanner.

The method of the invention may be used on individual pieces or meat or on containers of meat. When the invention is used on container of meat, for example standard sized boxes; the tenderness result is the average tenderness of the contents of the container of meat.

The method of the invention may further include processing the x-ray images or arrays of data to correct for instrumental effects.

The images or arrays of values produced by the x-ray scanner may be stored for future retrieval and/or processing. Additionally the tenderness values may also be stored for future retrieval.

EXAMPLES

Tenderization During Meat Aging

This example focused on the myofibrillar contributions on tenderness by controlling the ambient conditions during aging (Hopkins and Thompson, 2002). The shear force testing was performed using a MIRINZ shear force device. The MIRINZ device is similar to the better known Warner-Bratzler instrument but uses a different scale. Both scales are linearly related to each other (Graafhuis, A. E., Honikel, K. O., Devine, C. E. and Chrystall, B. B. 1991. Meat tenderness of different muscles cooked to different temperatures and assessed by different methods. Proc. 37th Int. Congress of Meat Science and Technology, Kulmbach, 365-368), where the shear force values measured with the Warner Bratzler shear device are approximately 0.65% of MIRINZ device values.

Eight beef striploins (beef longissimus muscle) were removed post rigor from electrically stimulated carcasses approximately 12 hours after slaughter and were then cut into two longitudinal pieces. Portions were about 150 mm long and ~20 mm thick with a cross-section of ~15,000 mm². One of each pair was kept at HortResearch at 15° C. and the other half was flown to the DEXA laboratory in Wellington, where it was also placed at 15° C. The controlled temperature enabled identical aging of the meat. Synchronously at HortResearch samples were taken from the beef LD for shear force testing and in the DEXA laboratory x-ray scans were made. The first measurements (defined as T=0 h) took place approximately 12 hours after slaughter at both locations. Thus, tenderization, which commences at rigor mortis, had already occurred from an original shear force of ~200 N to ~120 N (Devine, C. E. and Graafhuis, A. E., 1994. The basal tenderness of unaged lamb, Meat Science, 39, 285-291). During the highest rate of tenderization in the first 60 h after slaughter, 7 DEXA scans and 3 MIRINZ shear force tests were made, with an additional shear test after 114 hours (T=102 h).

Figure 3:
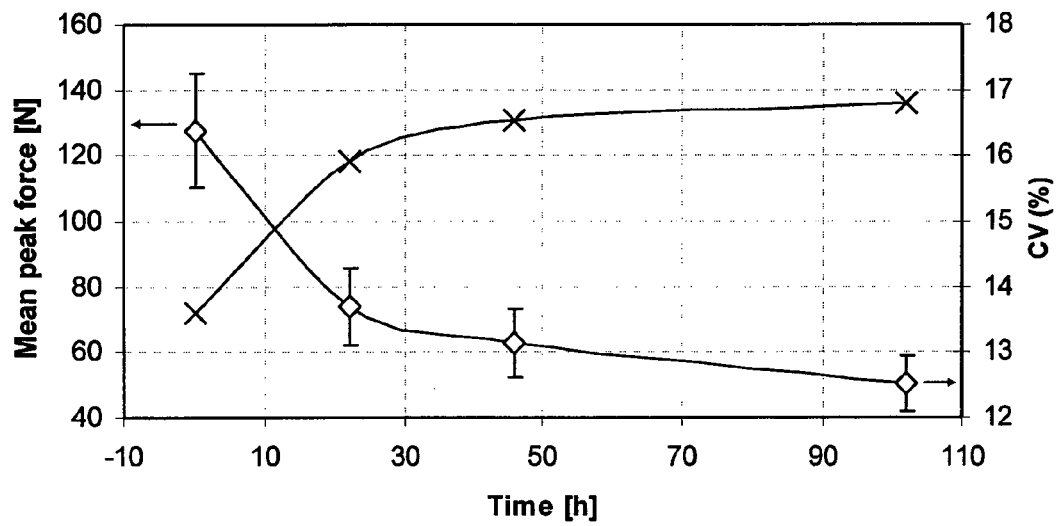
FIG. 3 is a graph of mean peak force (calculated mean from 10 shears per sample and time) against time for the first Example.

At given measurement times T the beef samples were frozen at −20° C. and cooked from the frozen state (to prevent tenderization while thawing slowly) in a water bath at 80° C. to reach an internal temperature of 75° C. Ten shear force measurements were obtained from each sample. The mean of the 10 shears was used for regression analysis with DEXA. FIG. 3 shows the average of the mean peak shear forces of the 8 steaks, including the average standard deviation for each steak, and the coefficient of variation CV (standard deviation/mean*100). In particular average measured peak shear forces (diamonds) at T=0, 21.75, 45.75, and 102 h are shown. Error bars represent the average standard deviations within the 8 steaks assessed at each point.

Standard deviations within steaks were large; ranging from 4 N (CV=7.5%) for Steak #5 at T=21.75 h, to 30 N (CV=27%) for Steak #2 at the same time. The average standard deviation was 12 N (CV=16%). While the standard deviation was decreasing during the course of the experiment, the CVs actually increased from 14% at T=0 h to 17% at T=102 h.

X-ray images, which included all eight steaks, required morphological rendering of the individual pieces. Segmentation occasionally necessitated excluding the borders of steaks in the image where individual pieces touched each other. Apart from that, standard segmentation procedures such as thresholding worked well. Raw image data of the individual pieces was extracted into a file for further analysis. The procedure was repeated for all images taken at given times.

Figure 4:
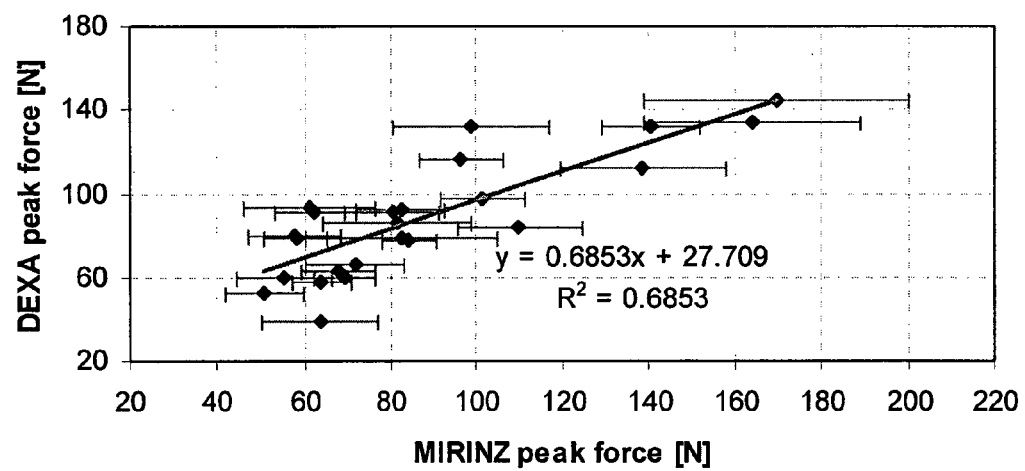
FIG. 4 is a scatter plot of shear forces predicted from DEXA parameters using multiple, non-linear regression and measured mean peak forces.
Figure 5:
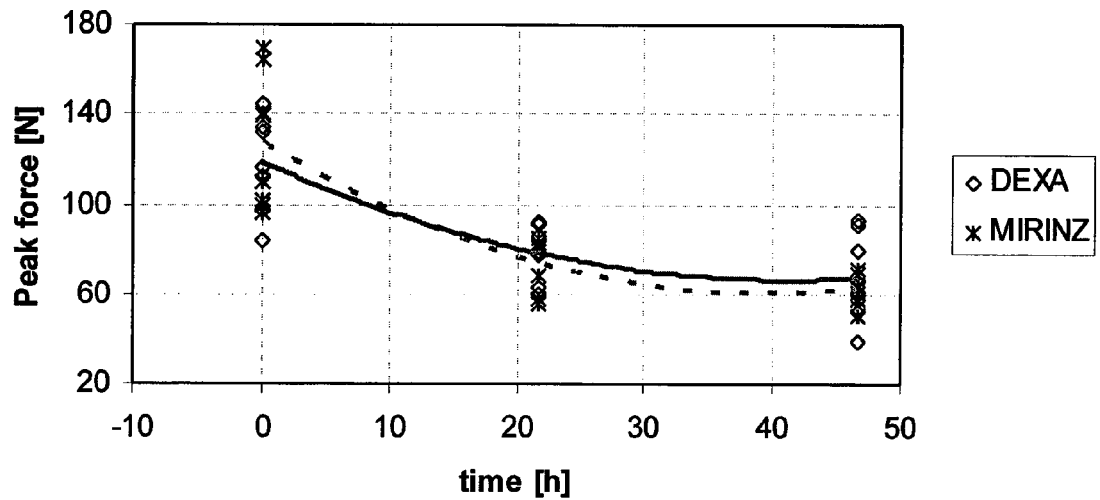
FIG. 5 is a graph showing measured and predicted (from FIG. 4) peak force variation over time.

Synchronous shear force tests and DEXA scans were performed at three times; T=0, 22.75, and 45.75 h; only these times were used for regression analysis. Best results were achieved when multiple regressions were executed. In FIG. 4 a multiple non-linear regression with a number of DEXA parameters gave a correlation coefficient of 0.69 in the resulting scatter plot of predicted and measured shear forces. The correlation coefficient is only indicative of the quality of a correlation and below 0.7 is often considered weak, but the large standard deviation of the shear force within steaks has to be considered. The error bars in FIG. 4 represent the standard deviations of the ten shears per sample, which are particularly large at higher mean peak force values. The error for DEXA is best represented by the scanner precision, which was evaluated for the machine used at 1.5% (state-of-the-art machines have precision below 1%). The resulting error bars do not exceed the size of the markers and were therefore omitted from the plot. The data from FIG. 4 was used in the peak force-time plot in FIG. 5. The trend lines in the plots follow a similar, non-linear decrease in tenderization over time, although the mechanical measurement is more pronounced.

Correlation Between Mean Shear Force and the Standard Deviation of Shear Force

Figure 6:
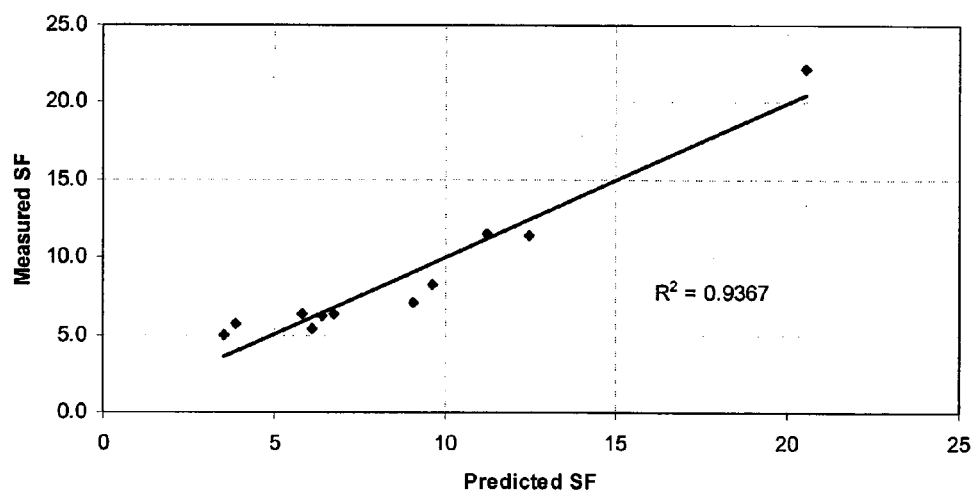
FIG. 6 is a graph showing the correlation between shear force and the standard deviation of shear force.

FIG. 6 shows the correlation between the standard deviation of the shear force and the mean shear force. In FIG. 6 a strip loin steak was tested to measure the mean shear force. The standard deviation of the shear force was also measured. As can be seen in FIG. 6 the standard deviation of the shear force is strongly correlated to the shear force. This means that instead of relating the transmitted x-rays to the shear force the transmitted x-rays can be related to the standard deviation of the shear force and the tenderness of the meat can be assessed from the standard deviation of the shear force.

Figure 7:
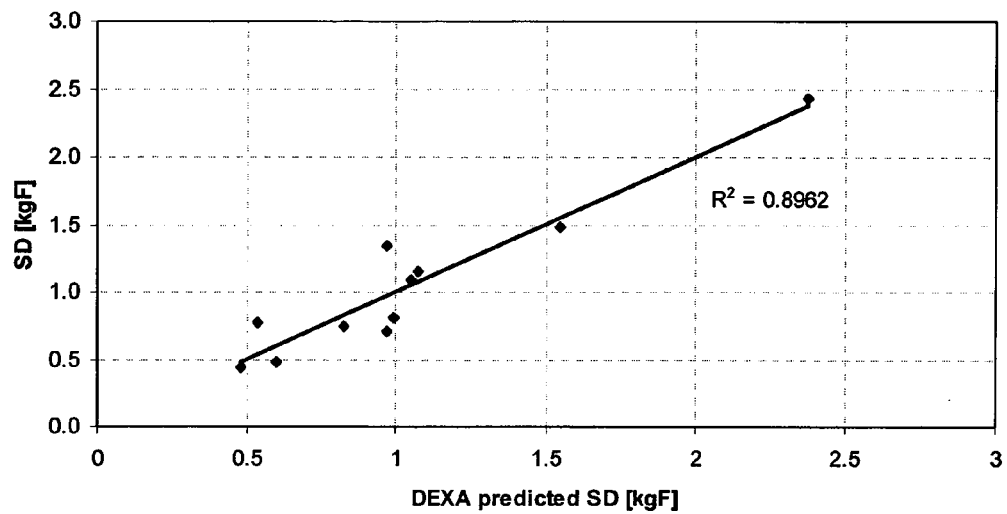
FIG. 7 is a graph showing the correlation between shear force and the standard deviation of shear force as determined using a DEXA device.

FIG. 7 shows the correlation between the calculated standard deviation of the shear force and the predicted standard deviation of the shear force using a DEXA device. The standard deviation of the measured means shear force was determined from a mean of ten shears on the strip loin steak used in FIG. 6. As can be seen in FIG. 7 there is a strong correlation between the calculated standard deviation of the mean shear force and the standard deviation of the means shear force predicted using a DEXA device.

FIGS. 6 and 7 show that tenderness can be predicted using an x-ray device arranged to predict the standard deviation of the mean shear force of the meat.

Prediction of Tenderness Using Single X-Ray Energies

Figure 8:
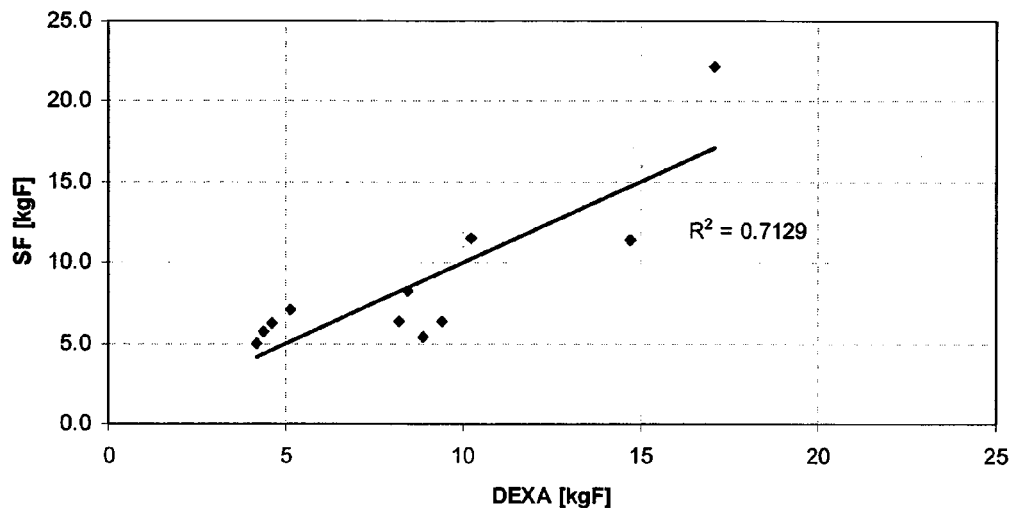
FIG. 8 is a graph showing the correlation between measured shear force and the shear force determined using one single x-ray energy parameter.

The previous examples have focused on the use of a dual energy x-ray absorption device. However the method and system of the invention also works with single energy x-ray devices. FIG. 8 shows the correlation between the calculated mean shear force and the measured mean shear force predicted using a single single-energy x-ray parameter. The trial was taken on a strip loin steak. As can be seen in FIG. 8 a single single-energy x-ray parameter can be correlated with the mean shear force and used to assess the tenderness of a sample of meat.

Figure 9:
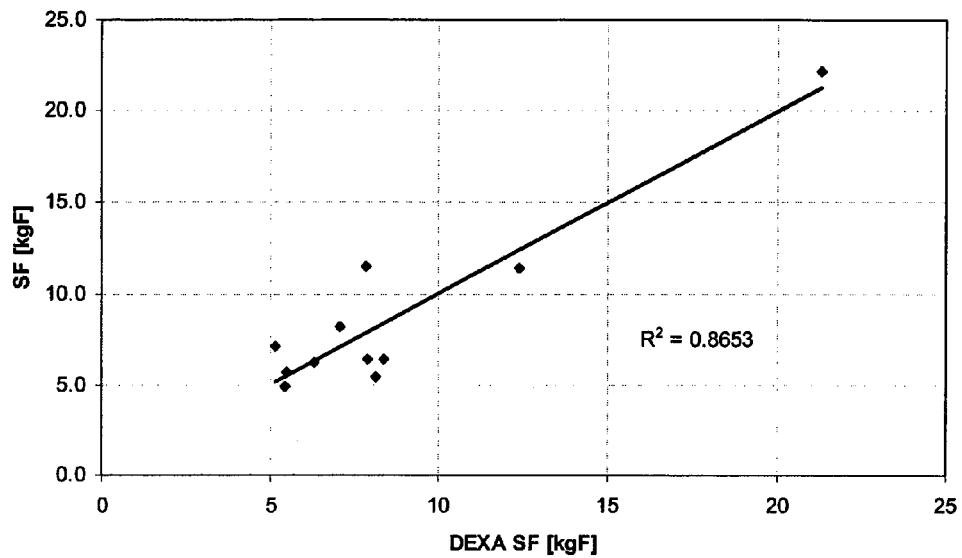
FIG. 9 is a graph showing the correlation between the measured shear force and the shear force determined using four single energy image parameters.

FIG. 9 shows the correlation between the mean shear force and the predicted shear force using four single energy x-ray parameters taken from a DEXA image. Again a strip loin steak was used for the trail. FIG. 9 shows that a plurality of single energy x-ray parameters can be correlated with the mean shear force and used to assess the tenderness of a sample of meat. Comparing FIGS. 8 and 9 it can be seen that a higher correlation between the calculated mean shear force and the predicted mean shear force when more single energy x-ray parameters are used. The examples given in FIGS. 8 and 9 use one and four single x-ray energy parameters respectively to predict the tenderness of meat; however, any number of single x-ray energy parameters can be used within the scope of the invention.

Multiple DEXA Images

Figure 10:
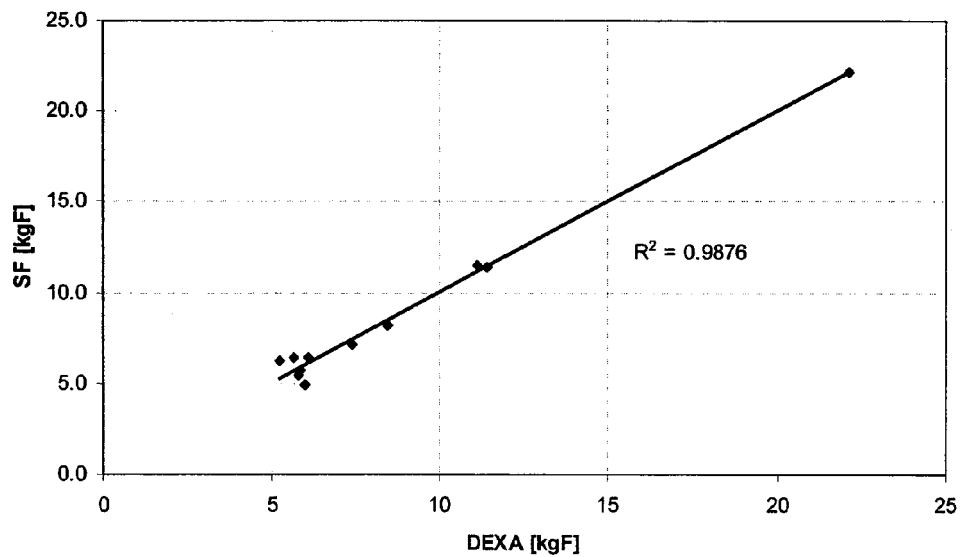
FIG. 10 is a graph showing the correlation between multiple DEXA image parameters and the measured mean shear force.
Figure 11:
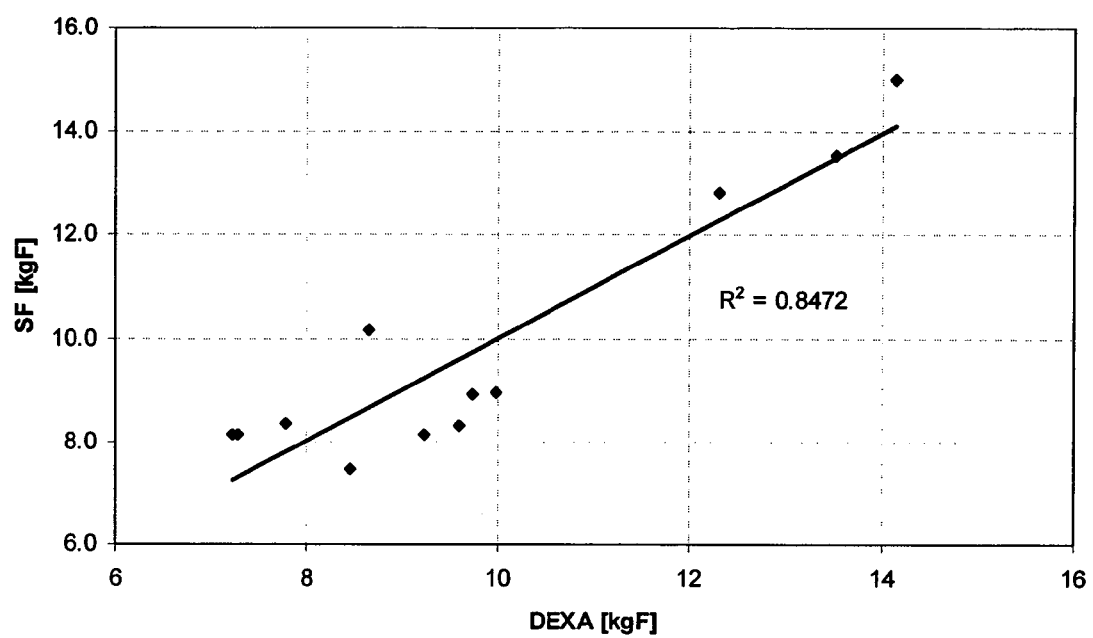
FIG. 11 is a graph showing the correlation between multiple DEXA image parameters and the measured mean shear force.

FIGS. 10 and 11 show examples where multiple DEXA images are correlated with the mean shear force as determined destructively. These figures show high correlation between the image and the shear force. FIGS. 10 and 11 indicate that assessing tenderness from multiple DEXA images will be successful.

INDUSTRIAL APPLICABILITY

As would be appreciated by one skilled in the art there are many possible applications for the invention.

The invention could be used for tenderness evaluation of individual pieces of meat. For instance, an end user retailer (such as a supermarket) may install such an apparatus and offer the information, perhaps combined with information on fat content, to the customer.

Another application would be in a meat processing plant, where meat is sorted and packed into quality classes depending on cut and fat content. Fat content can be assessed using earlier DEXA techniques, thus the same apparatus may be used. Tenderness could be additional information for quality classification. In this case the meat in the standard packing container could be assessed. Alternatively, the individual pieces may be evaluated for tenderness and an average calculated for the standard packing container.

The invention may be used anywhere where tenderness information is of interest, and various capacities of the apparatus can be specifically manufactured.

Where in the foregoing description reference has been made to elements or integers having known equivalents, then such equivalents are included as if they were individually set forth. The term "comprising" as used in this specification and claims means "consisting at least in part of". That is to say, when interpreting statements in this specification and claims which include "comprising", the features prefaced by this term in each statement all need to be present but other features can also be present. Related terms such as "comprise" and "comprised" are to be interpreted in a similar manner.

Although the invention has been described by way of example and with reference to particular embodiments, it is to be understood that modifications and/or improvements may be made without departing from the scope or spirit of the invention as defined in the accompanying claims.

The invention claimed is:

1. A method for assessing a tenderness of meat comprising the steps of:
scanning a sample of meat through an x-ray beam;
detecting or measuring a transmitted x-ray radiation through the meat sample;
relating the transmitted x-ray radiation to a characteristic of a shear force of the meat sample;
assessing the tenderness of the meat sample from the characteristic of the shear force,
and wherein the meat is scanned using a dual energy x-ray absorption scanner to produce two images or arrays of values representative of intensities of the x-rays at two energy levels,
the two images or arrays of values comprise a high energy image or array and a low energy image or array,
and the high and low energy images or arrays are applied via a regression equation of a general form:

$$PF = A \cdot f^n(I_L, I_H) + B \cdot f^m(\text{stdev}(r(I_L, I_H))) + C \cdot f^l(I_L) + D \cdot f^p(I_H) + E \quad (1)$$

where:
PF=the predicted peak force;
A, B, C, D, and E are constants; and
m, n, l, and p are integers;
$I_L$ is a low energy incident intensity of an x-ray beam; and
$I_H$ is a high energy incident intensity of an x-ray beam.

2. A method for assessing the tenderness of meat as claimed in claim 1 wherein the step of relating the transmitted x-ray radiation to the characteristic of the shear force of the meat sample is via a calculation of the characteristic of shear force, estimation of the characteristic of shear force or comparison with a previously determined characteristic of the shear force.

3. A method for assessing the tenderness of meat as claimed in claim 1 wherein the characteristic of shear force is one or more of shear force, a standard deviation of the shear force, a peak shear force, a mean shear force and an initial yield.

4. A method for assessing the tenderness of meat as claimed in claim 1 further including a pre-step of calibrating the x-ray scanner by correlating images to a measured shear force of the sample or of a representative sample.

5. A method for assessing the tenderness of meat as claimed in claim 1 wherein the high energy and low energy images or arrays are applied in such a way to calculate an objective tenderness expressed as shear force.

6. A method for assessing the tenderness of meat as claimed in claim 1 wherein the regression equation is applied and/or derived in a calibration step.

7. A method for assessing the tenderness of meat as claimed in claim 1 wherein the meat is x-ray scanned in raw state, at temperatures above freezing.

8. A method for assessing the tenderness of meat as claimed in claim 1 wherein the meat is scanned in a cooked state.

9. A method for assessing the tenderness of meat as claimed in claim 1 wherein the meat is scanned in a frozen state.

10. A method for assessing the tenderness of meat as claimed in claim 1 wherein a size of the meat is of optimum size with respect to an x-ray scanner configuration.

11. A method for assessing the tenderness of meat as claimed in claim 1 wherein individual pieces of meat are scanned.

12. A method for assessing the tenderness of meat as claimed in claim 1 wherein a container of meat is scanned and the tenderness is provided as an averaged result over the entire contents.

13. A method for assessing the tenderness of meat as claimed in claim 1 further including a step of correcting the assessment for instrumental effects that may affect the assessment of the tenderness of meat.

14. A method for assessing the tenderness of meat as claimed in claim 1 wherein the two images or arrays of values are stored for future retrieval and/or processing.

15. An apparatus for assessing a tenderness of meat comprising means for scanning a sample of meat through an x-ray beam;

means for detecting or measuring a transmitted x-ray radiation through the meat sample;

means for relating the transmitted x-ray radiation to a characteristic of the shear force of the meat sample;

means for assessing the tenderness of the meat sample from the characteristic of the shear force, and wherein the meat is scanned using a dual energy x-ray absorption scanner to produce two images or arrays of values representative of the intensities of the x-rays at two energy levels, the two images or arrays of values comprise a high energy image or array and a low energy image or array, and the high and low energy images or arrays are applied via a regression equation of the general form:

$$PF = A \cdot f^n(I_L, I_H) + B \cdot f^m(\text{stdev}(r(I_L, I_H))) + C \cdot f^l(I_L) + D \cdot f^p(I^p) + E \quad (1)$$

where:

PF = the predicted peak force;

A, B, C, D, and E are constants; and m, n, l, and p are integers:

$I_L$ is a low energy incident intensity of an x-ray beam; and $I_H$ is a high energy incident intensity of an x-ray beam.

16. An apparatus for assessing the tenderness of meat as claimed in claim 15 wherein the apparatus comprises or includes a dual energy x-ray absorption scanner for scanning the meat and arranged to produce two images or arrays of values representative of the intensities of the x-rays at two energy levels.

17. An apparatus for assessing the tenderness of meat as claimed in claim 15 wherein the associated computer system is arranged to store the images or arrays of values for future retrieval and/or processing.

* * * * *